(12) United States Patent
Sugiyama et al.

(10) Patent No.: US 8,066,683 B2
(45) Date of Patent: Nov. 29, 2011

(54) DISPOSABLE DIAPER

(75) Inventors: Katsuhiko Sugiyama, Tokyo (JP); Tomotsugu Miyoshi, Tokyo (JP); Izumi Tashiro, Tokyo (JP)

(73) Assignees: Oji Nepia Co., Ltd., Chuo-ku (JP); Oji Paper Co., Ltd., Chuo-Ku (JP)

( * ) Notice: Subject to any disclaimer, the term of this patent is extended or adjusted under 35 U.S.C. 154(b) by 1016 days.

(21) Appl. No.: 11/545,719

(22) Filed: Oct. 10, 2006

(65) Prior Publication Data

US 2007/0088302 A1   Apr. 19, 2007

(30) Foreign Application Priority Data

Oct. 14, 2005  (JP) ................................. 2005-300381

(51) Int. Cl.
*A61F 13/15* (2006.01)
*A61F 13/20* (2006.01)

(52) U.S. Cl. ............. 604/385.101; 604/367; 604/385.01

(58) Field of Classification Search .................. 604/367, 604/385.01, 385.101, 383
See application file for complete search history.

(56) References Cited

U.S. PATENT DOCUMENTS

| | | | | |
|---|---|---|---|---|
| 3,532,093 A | * | 10/1970 | Lovret | 604/348 |
| 6,527,756 B1 | * | 3/2003 | Mishima et al. | 604/385.19 |
| 6,960,197 B1 | * | 11/2005 | Gustafsson et al. | 604/348 |
| 7,396,350 B2 | * | 7/2008 | Mishima et al. | 604/385.28 |
| 2004/0039363 A1 | | 2/2004 | Sugiyama et al. | |

FOREIGN PATENT DOCUMENTS

| | | |
|---|---|---|
| GB | 2 268 073 | 1/1994 |
| JP | 09-510384 | 10/1997 |
| JP | 2002-011044 | 1/2002 |
| WO | 95/25493 | 9/1995 |

* cited by examiner

*Primary Examiner* — Michele M Kidwell
(74) *Attorney, Agent, or Firm* — Burr & Brown

(57) ABSTRACT

A disposable diaper is provided, including an absorber, a top sheet, a back sheet, and a skin contact sheet (SCS) disposed above the top sheet. The skin contact sheet is formed with a stool passing opening and a urine passing opening at a portion corresponding to a crotch part, and includes an SCS central region formed by extending a strip-shaped inter-opening region, which is sandwiched by the two openings and extends in the width direction, by half the length between the openings in the anterior direction and in the posterior direction; an SCS ventral region located at the ventral side from the SCS central region; and an SCS dorsal region located at the dorsal side from the SCS central region. A least the SCS central region has the stretching force in the width direction, and an inter-opening central region sandwiched by the two openings includes a non-stretchable region.

17 Claims, 7 Drawing Sheets

DISPOSABLE DIAPER

BACKGROUND OF THE INVENTION

1. Field of the Invention

The present invention relates to a disposable diaper which includes a top sheet, a back sheet, and an absorber and in which a skin contact sheet is disposed above the top sheet.

2. Description of the Related Art

In recent years, as a diaper for an infant or an elder or disabled person, there has been widely used a disposable diaper which includes an absorber, a top sheet disposed to cover the upper surface of the absorber and at least partially formed of a liquid permeable material, and a back sheet disposed to cover the lower surface of the absorber and formed of a liquid impermeable material. This disposable diaper is used in such a manner that a surface of the top sheet is applied to contact the skin of a wearer of the disposable diaper. Thereby, the urine discharged by the wearer penetrates through the top sheet and is absorbed and retained by the absorber. Further, the back sheet having good leakage preventing performance prevents the leakage of the excrement to the outside of the diaper.

In the disposable diaper of the above-described structure, however, the urine penetrates through the top sheet but most of the stool does not penetrate through the top sheet and thus remains thereon. The stool remaining on the top sheet adheres to the crotch or the buttocks of the wearer. This requires a troublesome wiping work, which increases the burden of child rearing or nursing care and causes skin trouble to the wearer. Such phenomenon becomes more prominent when the stool discharged by the wearer is an unformed stool.

In view of this, another type of disposable diapers has been proposed in which another sheet member (hereinafter referred to as a "skin contact sheet" in the present specification) is disposed above the top sheet (see Paragraph 0010 and FIG. 2 of Japanese Registered Utility Model No. 2559050, and Paragraph 0020 and FIG. 1 of Japanese Unexamined Patent Application Publication No. 2002-11044, for example). These disposable diapers are structured such that the skin contact sheet is formed with an opening capable of passing a stool therethrough (i.e., a stool passing opening) for causing the stool discharged by the wearer to drop on the top sheet through the opening.

According to the above-described disposable diaper, the skin contact sheet first contacts the skin of the wearer. Thus, the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer can be expected.

Usually, for such purposes as improvement of the close contact of the skin contact sheet with the skin of the wearer, the skin contact sheet is provided with a stretchable elastic member to form a stretchable region. Thus, the stretchable region is usually formed with a wavy gather by the stretchable elastic member. When pressed against the skin of the wearer, the thus formed gather causes uncomfortable feeling or pain to the wearer in some cases. In particular, in the case of a disposable diaper having the skin contact sheet formed with two openings (i.e., a stool passing opening and a urine passing opening), a region of the skin contact sheet corresponding to a crotch part and sandwiched between the two openings is strongly pressed by or frequently rubbed against the wearer. With the formation of the gather, therefore, the above-described pain or the like and the skin trouble tend to occur in this region. In this regard, the conventional disposable diaper is not satisfactory enough and still open to improvement.

SUMMARY OF THE INVENTION

As described above, a disposable diaper suppressing the direct contact of the discharged stool with the skin of the wearer and capable of suppressing the pain or the like occurring at the crotch part has not yet been disclosed so far, and thus has been longed for. In view of the conventional techniques as described above, it is an object of the present invention to provide a disposable diaper which suppresses the direct contact of the discharged stool with the skin of the wearer and is capable of suppressing the pain or the like occurring at the crotch part to thereby suppress the occurrence of skin trouble.

The present invention provides the following disposable diaper.

A disposable diaper according to a first aspect of the present invention is formed by a front body part, a crotch part, and a back body part, and includes an absorber, a top sheet disposed to cover an upper surface of the absorber and at least partially formed of a liquid permeable material, a back sheet disposed to cover a lower surface of the absorber and formed of a liquid impermeable material, and a skin contact sheet (SCS) disposed above the top sheet. The skin contact sheet is formed, at a portion thereof corresponding to the crotch part, with a stool passing opening capable of passing a stool therethrough and a urine passing opening capable of passing the urine therethrough. Further, the skin contact sheet includes an SCS central region, an SCS ventral region, and an SCS dorsal region. The SCS central region is formed by extending a strip-shaped region sandwiched by the two openings and extending in the width direction (i.e., an inter-opening region) by half the length between the openings in the anterior direction and in the posterior direction. The SCS ventral region is located at the ventral side from the SCS central region, and the SCS dorsal region is located at the dorsal side from the SCS central region. At least the SCS central region of the skin contact sheet has the stretching force in the width direction. Further, a region located between the two openings (i.e., an inter-opening central region) includes a region having no stretching force in the width direction and in the longitudinal direction (i.e., a non-stretchable region).

According to a second aspect of the present invention, in the disposable diaper according to the first aspect of the present invention, the non-stretchable region may be disposed to extend into a strip shape between the two openings at the center in the width direction of the inter-opening central region.

According to a third aspect of the present invention, in the disposable diaper according to either one of the first and second aspects of the present invention, the length in the width direction of the non-stretchable region may be 10 to 100% of the length in the width direction of the inter-opening central region.

According to a fourth aspect of the present invention, in the disposable diaper according to any one of the first to third aspects of the present invention, stretchable elastic members (i.e., opening stretchable members) may be disposed on a region of the skin contact sheet excluding the non-stretchable region to extend in the longitudinal direction. Further, each of the opening stretchable members may have a width-direction component at least in the SCS central region.

According to a fifth aspect of the present invention, in the disposable diaper according to any one of the first to fourth aspects of the present invention, the non-stretchable region of the skin contact sheet may be in a planar state.

According to a sixth aspect of the present invention, in the disposable diaper according to either one of the forth and fifth aspects of the present invention, the opening stretchable members of the skin contact sheet may be formed by disposing the stretchable elastic members so as to cross between the two openings (i.e., the urine passing opening and the stool passing opening) and to extend in the longitudinal direction, and thereafter cutting the stretchable elastic members at the crossed section.

The disposable diaper according to the present invention suppresses the direct contact of the discharged stool with the skin of the wearer, and effectively suppresses the pain or the like caused by the portion of the skin contact sheet corresponding to the crotch part to thereby effectively suppress the occurrence of the skin trouble. That is, the disposable diaper according to the present invention prevents the disadvantage of the disposable diaper provided with the skin contact sheet formed with the two openings and having the stretching force, and has a good effect of allowing comfortable use of the disposable diaper having the skin contact sheet formed with the two openings.

DETAILED DESCRIPTION OF INVENTION

Figure 1:
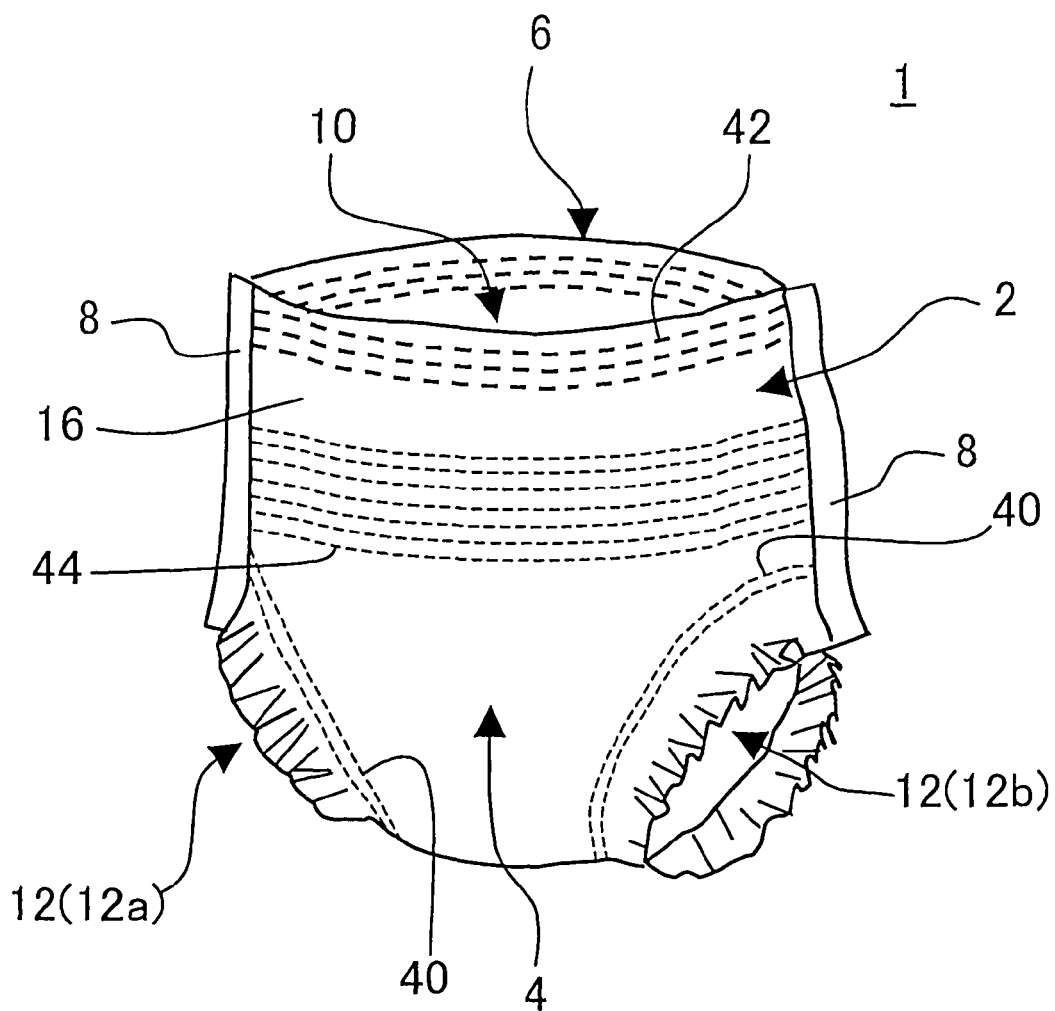
FIG. 1 is a schematic perspective view illustrating one embodiment of the disposable diaper according to the present invention, as viewed from the front side of the diaper.

Specific description will now be made of preferred embodiments of the disposable diaper according to the present invention, taking a two-piece-type and pants-type diaper as an example. The present invention, however, widely includes disposable diapers which have particular features of the invention, and thus is not limited to the following embodiments. For drawing convenience, leg-surrounding stretchable members are eliminated from the drawing of FIG. 3.

Figure 2:
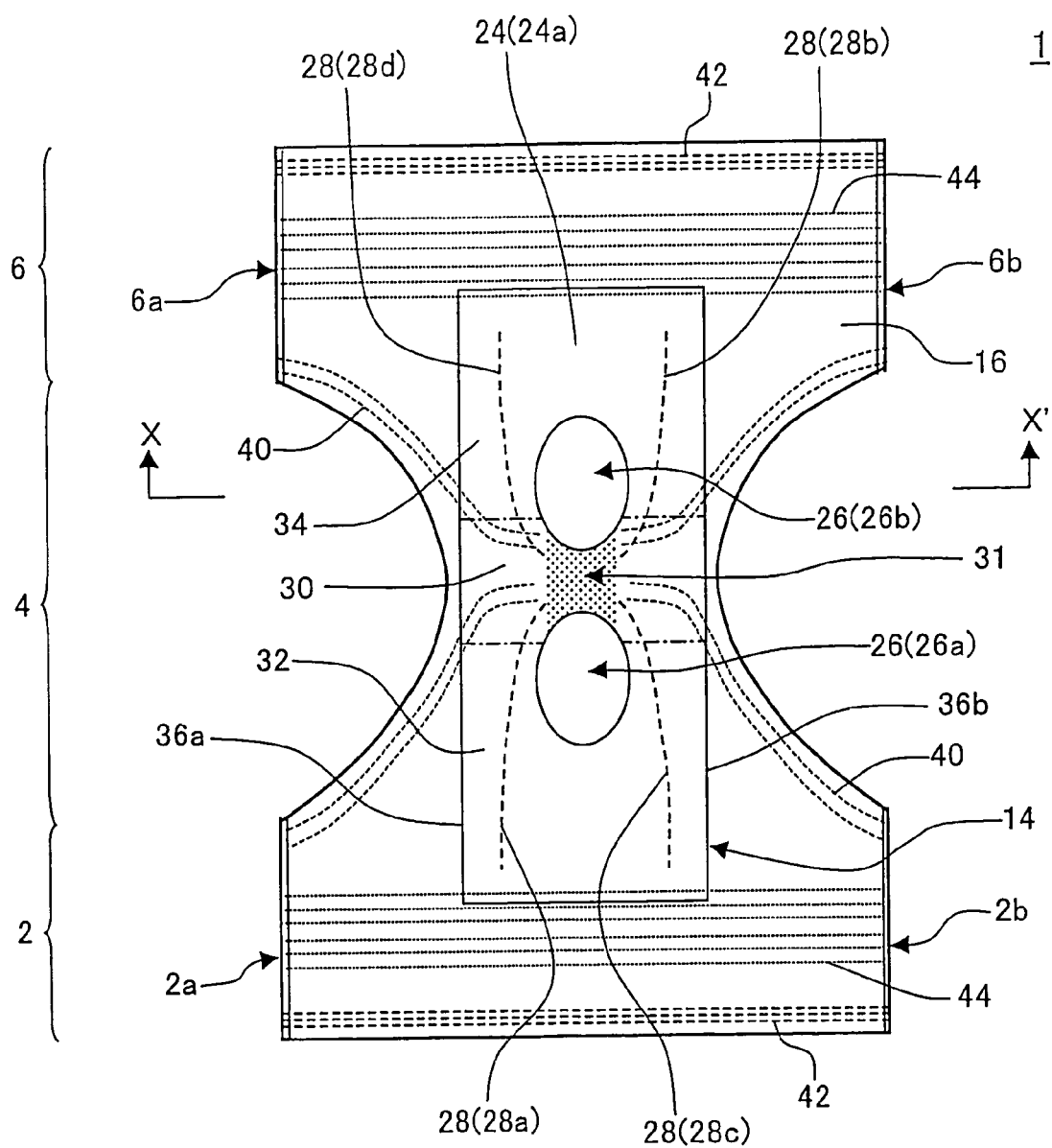
FIG. 2 is a plan view illustrating the one embodiment of the disposable diaper according to the present invention, as viewed from the side of the absorbent member of the disposable diaper shown in FIG. 1 when the diaper is unfolded.
Figure 3:
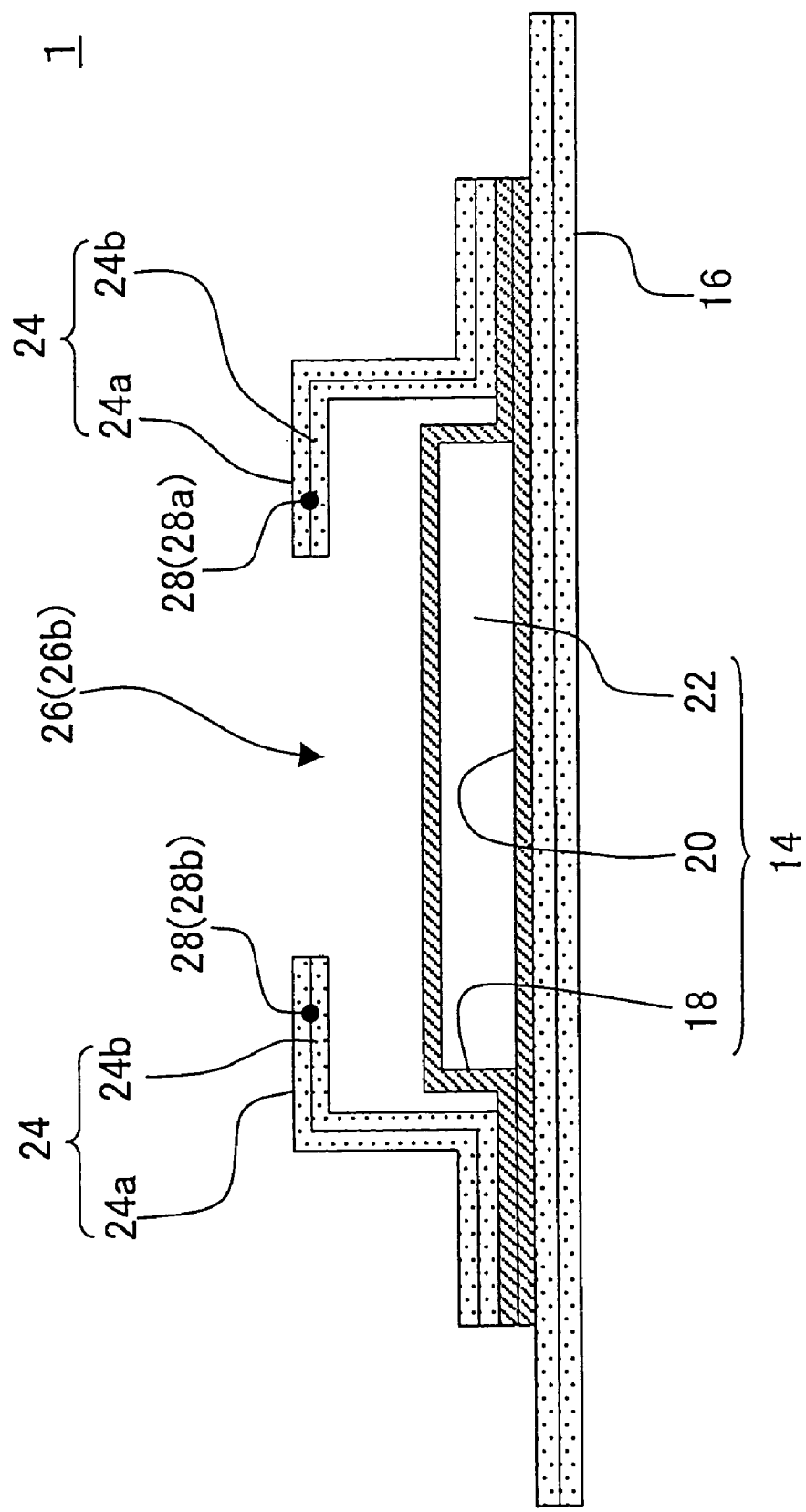
FIG. 3 is a schematic cross-sectional view illustrating the one embodiment of the disposable diaper according to the present invention, as cut along the X-X' line in the disposable diaper shown in FIG. 2.

In the present specification, the "pants-type diaper" refers to a diaper preformed into a pants shape, as in the case of a disposable diaper 1 illustrated in FIGS. 1 to 3, in which corresponding side edges of a front body part 2 and a back body part 6 (i.e., side edges 2a and 6a and side edges 2b and 6b) are joined together to form joining parts 8, a waist-surrounding opening 10, and a pair of leg-surrounding openings 12a and 12b. Further, the "two-piece-type diaper" refers to a type of diaper which includes an absorbent member 14 having a function of absorbing and retaining the excrement of a wearer of the diaper (i.e., an absorbing and retaining function) and an exterior covering member 16 having a function of covering the body of the wearer (i.e., a fitting function), and in which the absorbent member 14 is disposed on the inside of the exterior covering member 16. As illustrated in FIG. 3, the absorbent member 14 is a member including, as component parts thereof, an absorber 22, a top sheet 18, and a back sheet 20.

Further, in the present specification, the "front body part," the "crotch part," and the "back body part" refer to a part covering the ventral part (i.e., the front side of the body) of a wearer when the diaper is applied to the wearer, a part covering the crotch of a wearer when the diaper is applied to the wearer, and a part covering the dorsal part (i.e., the back side of the body) of a wearer when the diaper is applied to the wearer, respectively.

[1] The structure of the disposable diaper according to the present invention: As in the case of the disposable diaper 1 illustrated in FIGS. 1 to 3, the disposable diaper according to the present invention is a disposable diaper including the absorber 22, the top sheet 18 disposed to cover the upper surface of the absorber 22 and at least partially formed of a liquid permeable material, and the back sheet 20 disposed to cover the lower surface of the absorber 22 and formed of a liquid impermeable material. The disposable diaper is formed by the front body part 2, a crotch part 4, and the back body part 6, and further includes a skin contact sheet (SCS) 24 which is disposed above the top sheet 18. The skin contact sheet 24 is formed, at a portion thereof corresponding to the crotch part 4, with a stool passing opening 26 (26b) capable of passing a stool therethrough and a urine passing opening 26 (26a) capable of passing the urine therethrough. Further, the skin contact sheet 24 includes a skin contact sheet central region (an SCS central region) 30, a skin contact sheet ventral region (an SCS ventral region) 32, and a skin contact sheet dorsal region (an SCS dorsal region) 34. The SCS central region 30 is formed by extending a strip-shaped region (i.e., an inter-opening region) 29, which is sandwiched by the two openings 26 (26a and 26b) and extends in the width direction, by half a length 29a (see FIG. 4) between the openings in the anterior direction and in the posterior direction. The SCS ventral region 32 is located at the ventral side from the SCS central region 30, and the SCS dorsal region 34 is located at the dorsal side from the SCS central region 30. At least the SCS central region 30 of the skin contact sheet 24 has the stretching force in the width direction. Further, a region located between the two openings 26 (26a and 26b) (i.e., an inter-opening central region) 35 includes a region which does not have the stretching force in the width direction and in the longitudinal direction (i.e., a non-stretchable region) 31. The "region formed by extending the inter-opening region 29 in the anterior direction and in the posterior direction" here refers to a region formed by increasing the length in the longitudinal direction of the inter-opening region 29 by a predetermined length both in the direction of the front body part (i.e., in the direction of the front side of the diaper) and in the direction of the back body part (i.e., in the direction of the back side of the diaper), with the length in the width direction of the inter-opening region 29 kept to be a constant value. Further, the longitudinal direction refers to the anteroposterior direction when the disposable diaper is applied to the wearer, while the width direction refers to the lateral direction when the disposable diaper is applied to the wearer. Furthermore, the width refers to the length in the width direction.

In the present embodiment, two points located on the maximum width and on the outer circumference of each of the two openings 26 (26a and 26b), i.e., points 33a and 33b located on the maximum width of the opening 26a and points 33c and 33d located on the maximum width of the opening 26b can be connected with the corresponding two points such that obtained line segments do not cross between the openings. A region encompassed by the thus obtained two line segments 36a (i.e., a line segment connecting the points 33a and 33d each located on the maximum width of the corresponding opening) and 36b (i.e., a line segment connecting the points 33b and 33d each located on the maximum width of the corresponding opening) and the two openings 26a and 26b is referred to as the inter-opening central region 35.

Further, in the present embodiment, the urine passing opening 26a is one of the two openings 26 located at the ventral side of the wearer, when the diaper is applied to the wearer. Meanwhile, the stool passing opening 26b is the other one of the two openings 26 located at the dorsal side of the wearer, when the diaper is applied to the wearer. Furthermore, the stretching force refers to a value (g/cm) obtained by dividing the force required to stretch the skin contact sheet of a certain width to full length in the vertical direction with respect to the width, by the width. In this case, the "certain width" may be the width in either the width direction or the longitudinal direction of the skin contact sheet. Therefore, if the above "certain width" refers to the width in the width direction of the skin contact sheet, the stretching direction is the longitudinal direction of the skin contact sheet. Meanwhile, if the "certain width" refers to the width in the longitudinal direction of the skin contact sheet, the stretching direction is the width direction of the skin contact sheet. There is no particular restriction on the length of the "certain width." Once the region to be measured and the stretching direction are determined, the length of the "certain width" is the length in the vertical direction with respect to the stretching direction of the region. Further, "to stretch the skin contact sheet to full length" refers to a state in which the contracted skin contact sheet is stretched to return to the original shape (i.e., length) of a sheet material (e.g., a nonwoven fabric) forming the skin contact sheet. Therefore, the above state does not include a state in which the skin contact sheet is further stretched to make the sheet material larger than its original shape. The stretching force is measured by a pull testing machine, and the intensity of the skin contact sheet is measured in the state in which the contracted skin contact sheet is stretched to full length. As the pull testing machine, a machine under the trade name of STROGRAPH manufactured by Toyo Seiki Seisaku-sho, Ltd. or a machine under the trade name of TENSILON manufactured by Orientec Co., Ltd. can be used. The recorded intensity is the value measured before the sheet has been stretched to full length to indicate the intensity of the nonwoven fabric. In the measurement of the stretching force, a region to be measured is cut out as a sample used in the measurement, and the stretching force of the region is measured with the region stretched in the vertical direction with respect to the above-described "certain width."

For example, when the stretching force of the SCS central region 30 or the non-stretchable region 31 is measured, a region to be measured is cut out from the skin contact sheet 24 as a sample used in the measurement. To measure the stretching force in the width direction, the stretching force is measured with opposite ends of the region in the width direction (i.e., the direction corresponding to the width direction of the skin contact sheet) held and stretched in the width direction. Meanwhile, to measure the stretching force in the longitudinal direction, the stretching force is measured with opposite ends of the region in the longitudinal direction (i.e., the direction corresponding to the longitudinal direction of the skin contact sheet) held and stretched in the longitudinal direction.

As described above, the inter-opening central region 35 of the skin contact sheet 24 includes the non-stretchable region 31. Thus, when the disposable diaper 1 is applied to the wearer, a large gather is not formed in the non-stretchable region 31 located between the two openings (i.e., the urine passing opening 26a and the stool passing opening 26b) of the skin contact sheet 24. Accordingly, the pain or the like and the skin trouble caused by the portion of the skin contact sheet 24 corresponding to the crotch part can be effectively suppressed.

[1-1] The skin contact sheet: The skin contact sheet is a member for separating the skin of the wearer from the top sheet, and is disposed above the top sheet. With the provision of the skin contact sheet, the skin of the wearer first contacts the skin contact sheet, and thus the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer is obtained.

As the material forming the skin contact sheet, a nonwoven fabric, a mesh sheet, a film, or the like made of such a resin as polyethylene, polypropylene, or polyester can be used, for example. In particular, it is preferable to use the nonwoven fabric for the good texture against the skin. The above-described materials may be liquid permeable, liquid impermeable, or water repellent. It is preferable, however, that the above-described materials are water repellent materials (e.g., a water repellent nonwoven fabric) for the ability to maintain dry texture (i.e., dryness) even after a long time wearing. Further, it is preferable that the skin contact sheet is a breathable sheet. Accordingly, an area (i.e., skin) in contact with the skin contact sheet is further prevented from becoming stuffy, and the occurrence of the skin trouble can be suppressed. The breathability of the breathable sheet is for letting out moisture evaporated from the body and for preventing the inside of the diaper from becoming stuffy. The degree of the breathability can be expressed in the moisture permeability measured by JIS Z 0208 "testing methods for determination of the water vapour transmission rate of moisture-proof packaging materials." It is preferable that the moisture permeability is within a range of 2000 to 10000 $g/m^2/24$ hr.

As illustrated in FIG. 2, to allow the passage of the urine and the stool discharged by the wearer, the skin contact sheet 24 is formed with the two openings (i.e., the urine passing opening 26a and the stool passing opening 26b). With this structure, the urine and the stool discharged by the wearer drop on the top sheet through the urine passing opening 26a and the stool passing opening 26b, respectively. Accordingly, the chance of direct contact of the urine and the stool with the skin of the wearer can be substantially decreased.

There is no particular restriction on the shape of the stool passing opening 26b, as long as the shape allows the passage of the stool. That is, the "opening" capable of passing the stool therethrough includes the so-called opening (i.e., hole) such as a circular opening, an oval opening, and a rhombic opening, and also includes a slit such as a cross-shaped slit and a star-shaped slit formed by crossing three or more slits. Further, a hole and a slit may be combined. In particular, it is preferable to use an oval opening or a star-shaped slit whose long axis direction is the anteroposterior direction (i.e., the longitudinal direction) of the diaper. The oval opening has an advantage of allowing the stool to easily pass through the opening of the skin contact sheet. Meanwhile, the star-shaped slit has an advantage of effectively preventing the stool once dropped on the top sheet through the opening of the skin contact sheet from being exposed again from the opening of the skin contact sheet and staining the buttocks of the wearer. For example, the disposable diaper 1 illustrated in FIG. 2 is an example in which a portion of the skin contact sheet 24 corresponding to the crotch part 4 of the diaper is formed with oval openings whose long axis direction is the anteroposterior direction of the diaper, as the urine passing opening 26a and the stool passing opening 26b. It is preferable to locate each of the urine passing opening 26a and the stool passing opening 26b at the center in the width direction of the skin contact sheet 24. There is no particular restriction on the location of each of the urine passing opening 26a and the stool passing opening 26b on the skin contact sheet 24 in the longitudinal direction, as long as the location allows the urine passing opening 26a to pass the urine therethrough or allows the stool passing opening 26b to pass the stool therethrough. Further, there is no particular restriction on the size of the urine passing opening 26a, as long as the size allows the passage of the urine. Similarly, there is no particular restriction on the size of the stool passing opening 26b, as long as the size allows the passage of the stool. For example, in an infant diaper of a large size (i.e., approximately 420 mm in length in the longitudinal direction), it is preferable that each of the urine passing opening 26a and the stool passing opening 26b is 50 to 150 mm in length in the longitudinal direction of the skin contact sheet 24, and 1 to 100 mm in length in the width direction of the skin contact sheet 24.

In the present invention, the SCS central region 30 of the skin contact sheet 24 has the stretching force in the width direction. Accordingly, when the disposable diaper 1 is applied to the wearer, the SCS central region 30 located between the two openings 26 (i.e., the urine passing opening 26a and the stool passing opening 26b) of the skin contact sheet 24 comes into close contact with the wearer, without becoming slack. Thus, the urine and the stool definitely pass through the respective openings and drop on the top sheet. Therefore, the urine and the stool can be effectively prevented from remaining on the skin contact sheet. It is preferable that the stretching force in the width direction of the SCS central region 30 is 2 to 20 g/cm, and more preferably 5 to 10 g/cm.

Further, in the present invention, the inter-opening central region 35 includes the non-stretchable region 31, as described above. The non-stretchable region refers to a region which does not have the stretching force both in the width direction and in the longitudinal direction. The stretching force of the non-stretchable region 31 is 0 g/cm. With the non-stretchable region 31 thus formed within the inter-opening central region 35, the non-stretchable region 31 is not formed with the gather. Thus, it is possible to suppress the pain or the like and the skin trouble caused by the region of the skin contact sheet 24 corresponding to the crotch part. It is preferable that the non-stretchable region 31 is not formed with the gather, as described above, and that the non-stretchable region 31 does not have many irregularities. It is further preferable that the non-stretchable region 31 is formed to be in a planar state. The planar state refers to a state in which the sheet material is flat, not formed with the gather.

Figure 4:
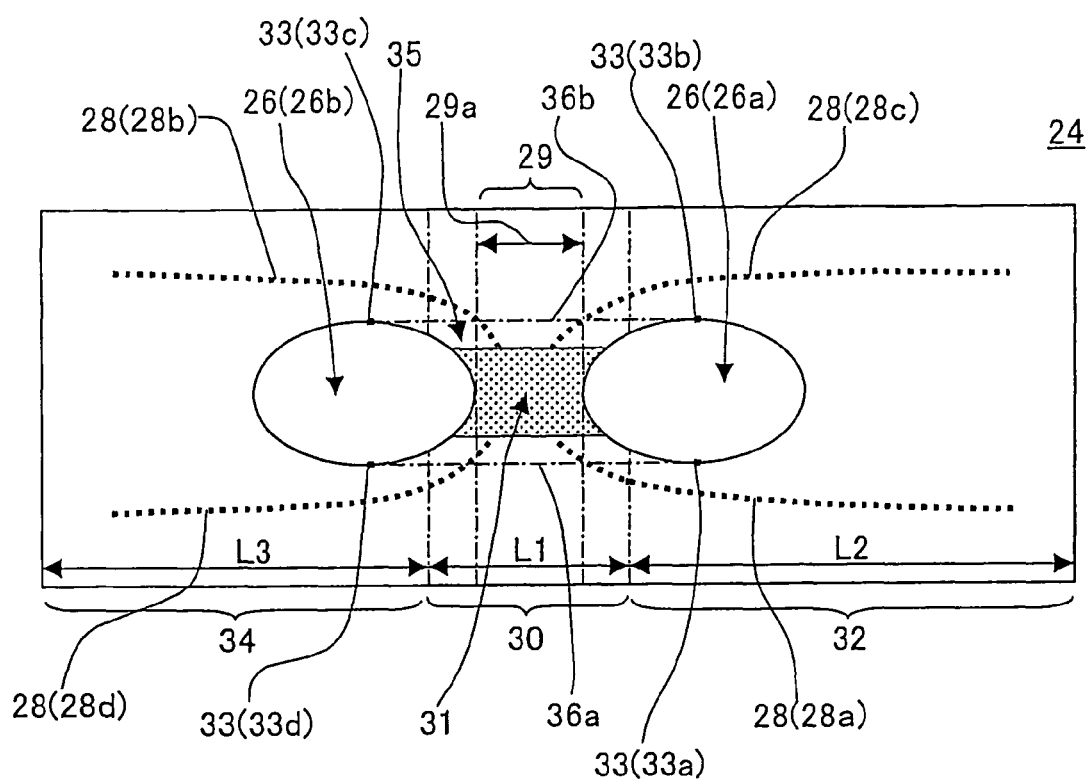
FIG. 4 is a schematic plan view illustrating the skin contact sheet used in the one embodiment of the disposable diaper according to the present invention.

FIG. 4 is a plan view schematically illustrating the skin contact sheet used in the disposable diaper according to the present embodiment. In the present embodiment, as illustrated in FIG. 4, the non-stretchable region 31 is located at the center in the width direction of the inter-opening central region 35 to extend into a strip shape between the two openings 26 (26a and 26b). Therefore, when the wearer puts on the disposable diaper according to the present embodiment, and even if the skin contact sheet is moved in the anteroposterior direction, the non-stretchable region can be kept in contact with the crotch of the wearer. Accordingly, the skin trouble and the like can be effectively suppressed. Further, it is preferable that the length in the width direction of the non-stretchable region 31 is 10 to 100% of the length in the width direction of the inter-opening central region 35, and that at least the central region of the inter-opening central region 35 is a non-stretchable region. With this structure, even if the skin contact sheet is moved in the lateral direction of the wearer, the non-stretchable region can be kept in contact with the crotch of the wearer, and the skin trouble can be more effectively suppressed.

In the present embodiment, as illustrated in FIG. 4, stretchable elastic members (i.e., opening stretchable members) 28 are stretchably provided at predetermined positions on the skin contact sheet 24. Therefore, the SCS central region has the stretching force in the width direction, and the inter-opening central region includes the non-stretchable region. That is, in the present embodiment, to form the non-stretchable region 31 within the SCS central region 30, four opening stretchable members 28 (28a, 28b, 28c, and 28d) are provided such that one end of each of the four opening stretchable members 28 is located in the SCS central region 30, and that each of the four opening stretchable members 28 extends in the longitudinal direction from the SCS central region 30 toward the SCS ventral region 32 or the SCS dorsal region 34. The non-stretchable region 31 is a region encompassed by a straight line connecting the end of the opening stretchable member 28a and the end of the opening stretchable member 28d in the SCS central region 30, a straight line connecting the end of the opening stretchable member 28b and the end of the opening stretchable member 28c in the SCS central region 30, and the two openings 26 (26a and 26b). With the opening stretchable members 28 thus provided, a region not provided with the opening stretchable members 28 (28a, 28b, 28c and 28d), i.e., the non-stretchable region 31 is formed within the SCS central region. The non-stretchable region 31 may be formed by providing four opening stretchable members so as not to be connected with one another between the two openings (i.e., the urine passing opening 26a and the stool passing opening 26b), or by providing two opening stretchable members so as to cross between the two openings (i.e., the urine passing opening 26a and the stool passing opening 26b) and to extend in the longitudinal direction and thereafter cutting the two opening stretchable members at the crossed section and performing a snapback operation. Alternatively, the non-stretchable region may be formed by pasting an additional sheet material, such as a nonwoven fabric, to the crossed section for offsetting the stretching force applied by the opening stretchable members.

Figure 5:
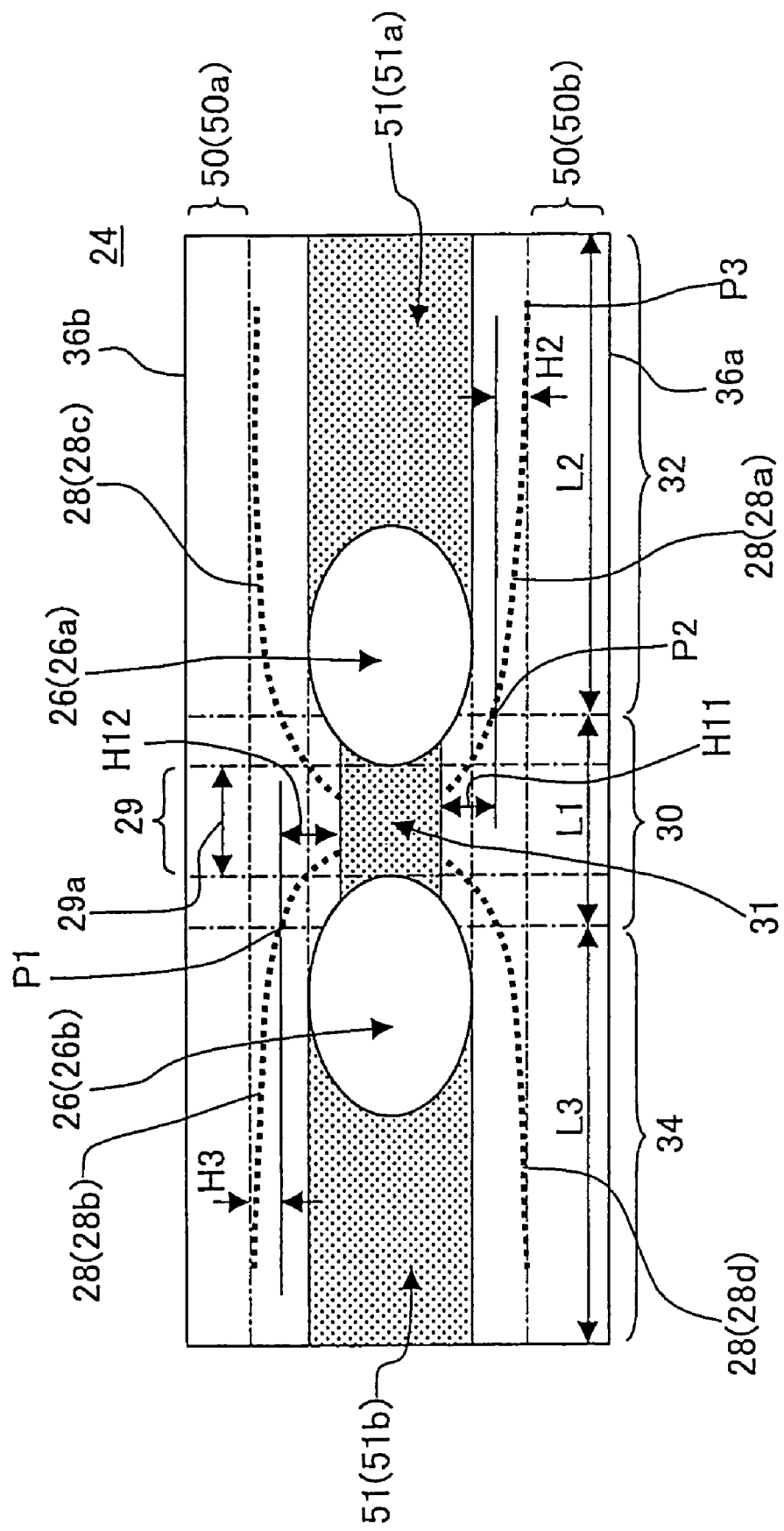
FIG. 5 is another schematic plan view illustrating the skin contact sheet used in the one embodiment of the disposable diaper according to the present invention.

As illustrated in FIG. 5, each of the four opening stretchable members 28 (28a, 28b, 28c and 28d) has a width-direction component in the SCS central region 30 so that the SCS central region 30 has the stretching force in the width direction. For example, the opening stretchable member 28a has a width-direction component H11 in the SCS central region 30, and the opening stretchable member 28b has a width-direction component H12 in the SCS central region 30. In this way, it is preferable in the present invention that the opening stretchable members 28 are provided to extend in the longitudinal direction in the region of the skin contact sheet 24 excluding the non-stretchable region 31, and that each of the opening stretchable members 28 has the width-direction component at least in the SCS central region 30. FIG. 5 in the above is a plan view schematically illustrating the skin contact sheet used in an embodiment of the disposable diaper according to the present invention.

In the disposable diaper having the skin contact sheet formed with two openings, the stool or the urine remains on the skin contact sheet without passing through the corresponding opening in some cases. This is because the portion of the skin contact sheet between the two openings becomes slack and the skin contact sheet fails to come in close contact with the body of the wearer. As a result, the position of each of the openings is not fixed, and the stool or the urine is discharged at a position deviant from the corresponding opening to drop on the skin contact sheet. To make the urine and the stool definitely pass through the respective openings to drop on the top sheet, it is preferable that the stretching force in the width direction of the SCS central region 30 is larger than each of the stretching force in the width direction of the SCS ventral region 32 and the stretching force in the width direction of the SCS dorsal region 34. Accordingly, when the disposable diaper 1 is applied to the wearer, the SCS central region 30 located between the two openings (i.e., the urine passing opening 26a and the stool passing opening 26b) of the skin contact sheet 24 comes in close contact with the wearer, without becoming slack. As a result, the urine and the stool definitely pass through the respective openings to drop on the top sheet, and the urine and the stool can be effectively prevented from remaining on the skin contact sheet. It is preferable that the stretching force in the width direction of the SCS central region is 1.1 to 5 times, more preferably 1.5 to 3 times, as large as each of the stretching force in the width direction of the SCS ventral region and the stretching force in the width direction of the SCS dorsal region. With the stretching force of the SCS central region set in the above range, the close contact of the skin contact sheet with the body of the wearer can be further improved. Further, as described above, it is preferable that the stretching force in the width direction of the SCS central region is 2 to 20 g/cm, and more preferably 5 to 10 g/cm. With the stretching force in the width direction of the SCS central region set in the above range, the skin contact sheet comes in close contact with the wearer to an appropriate extent.

To form the skin contact sheet 24 as described above, it is preferable to arrange the stretchable elastic members at the predetermined positions, as illustrated in FIGS. 2 and 5. That is, when L1, L2, and L3 represent the length in the longitudinal direction of the SCS central region 30, the length in the longitudinal direction of the SCS ventral region 32, and the length in the longitudinal direction of the SCS dorsal region 34, respectively, it is preferable that the quotient obtained by dividing the sum of the width-direction components (i.e., lengths) of the stretchable elastic members 28 in the SCS central region by L1 is larger than each of the quotient obtained by dividing the sum of the width-direction components (i.e., lengths) of the stretchable elastic members 28 in the SCS ventral region 32 by L2 and the quotient obtained by dividing the sum of the width-direction components (i.e., lengths) of the stretchable elastic members 28 in the SCS dorsal region 34 by L3. Accordingly, the stretching force in the width direction of the SCS central region can be made larger than the stretching force in the width direction of each of the SCS ventral region and the SCS dorsal region.

In the skin contact sheet 24 illustrated in FIG. 5, each of the four opening stretchable members 28a, 28b, 28c, and 28d has the width-direction component in the SCS central region 30. The sum of the width-direction components in the SCS central region refers to the sum of the width-direction component (i.e., length) H11 of the opening stretchable member 28a in the SCS central region 30, the width-direction component (i.e., length) H12 of the opening stretchable member 28b in the SCS central region 30, the width-direction component (i.e., length) of the opening stretchable member 28c in the SCS central region 30, and the width-direction component (i.e., length) of the opening stretchable member 28d in the SCS central region 30 (i.e., the sum of central region widths). When P2 indicates an intersection point of the borderline between the SCS central region 30 and the SCS ventral region 32 and the opening stretchable member 28a, the width-direction component (i.e., length) H11 represents the distance in the width direction from P2 to the end of the opening stretchable member 28a located in the SCS central region 30. Meanwhile, when P1 indicates an intersection point of the borderline between the SCS central region 30 and the SCS dorsal region 34 and the opening stretchable member 28b, the width-direction component (i.e., length) H12 represents the distance in the width direction from P1 to the end of the opening stretchable member 28b located in the SCS central region 30. The width-direction component of each of the opening stretchable members 28c and 28d in the SCS central region 30 is similarly defined.

Further, as illustrated in FIG. 5, when P2 indicates the intersection point of the borderline between the SCS central region 30 and the SCS ventral region 32 and the opening stretchable member 28a, and P3 indicates a point of the opening stretchable member 28a in the SCS ventral region 32 closest to an SCS side end 37a, a width-direction component (i.e., length) H2 of the opening stretchable member 28a in the SCS ventral region 32 is the distance in the width direction from P2 to P3. Similarly, a width-direction component (i.e., length) of the opening stretchable member 28c in the SCS ventral region 32 is the distance in the width direction from the intersection point of the borderline between the SCS central region 30 and the SCS ventral region 32 and the opening stretchable member 28c to a point of the opening stretchable member 28c in the SCS ventral region 32 closest to an SCS side end 37b. Therefore, the sum of the width-direction components (i.e., lengths) of the two opening stretchable members 28a and 28c in the SCS ventral region 32 refers to the total length of the width-direction component (i.e., length) H2 of the opening stretchable member 28a in the SCS ventral region 32 and the width-direction component (i.e., length) of the opening stretchable member 28c in the SCS ventral region 32 (i.e., the sum of ventral region widths).

Further, similarly to the above case of the SCS ventral region 32, the sum of the width-direction components (i.e., lengths) of the two opening stretchable members 28b and 28d in the SCS dorsal region 34 refers to the total length of a width-direction component (i.e., length) H3 of the opening stretchable member 28b in the SCS dorsal region 34 and the width-direction component (i.e., length) of the opening stretchable member 28d in the SCS dorsal region 34 (i.e., the sum of dorsal region widths).

Further, when L1, L2, and L3 represent the length in the longitudinal direction of the SCS central region 30, the length in the longitudinal direction of the SCS ventral region 32, and the length in the longitudinal direction of the SCS dorsal region 34, respectively, it is preferable that the quotient obtained by dividing the above sum of central region widths by L1 is larger than each of the quotient obtained by dividing the above sum of ventral region widths by L2 and the quotient obtained by dividing the above sum of dorsal region widths by L3. With this configuration, the stretching force in the width direction of the SCS central region 30 can be made larger than each of the stretching force in the width direction of the SCS ventral region 32 and the stretching force in the width direction of the SCS dorsal region 34. Accordingly, it is possible to make the SCS central region 30 come into close contact with the wearer, without becoming slack.

In the disposable diaper having the skin contact sheet, the more closely the skin contact sheet comes in contact with the body of the wearer, the more easily the stool and the urine pass through the respective openings. Thus, the effect of decreasing the chance of contact between the stool and the skin of the wearer can be obtained more easily. However, as the degree of close contact between the skin contact sheet and the body of the wearer increases, the space between the skin contact sheet and the skin of the wearer easily becomes stuffy due to the sweat or the like. Thus, the skin trouble tends to occur. To prevent such a state, as illustrated in FIG. 5, it is preferable in the skin contact sheet used in the disposable diaper according to the present invention that regions of the skin contact sheet 24 outside the two openings 26 in the longitudinal direction (i.e., opening outside regions) 51 (51a and 51b) are regions which do not have the stretching force in the width direction and in the longitudinal direction. In this way, with the two opening outside regions 51 (51a and 51b) of the skin contact sheet 24 having no stretching force in the width direction and in the longitudinal direction, the skin contact sheet does not come into close contact with the skin of the wearer in the regions having no stretching force. It is therefore possible to improve the breathability and to suppress the skin trouble.

As illustrated in FIG. 5, to form the two opening outside regions 51a and 51b of the skin contact sheet 24 as the regions which does not have the stretching force in the longitudinal direction and in the width direction, it is preferable that the two opening outside regions 51a and 51b are not provided with the opening stretchable members. It is preferable to provide the opening stretchable members 28 (28a, 28b, 28c, and 28d) so as to extend along the urine passing opening 26a and the stool passing openings 26b in the SCS central region 30 of the skin contact sheet 24 and to extend in the longitudinal direction in the SCS ventral region 32 and the SCS dorsal region 34. In this way, it is preferable to use linear stretchable elastic members as the opening stretchable members. Alternatively, the sheet material forming the skin contact sheet may be provided with elasticity.

Further, it is preferable in the present invention that two regions each extending into a strip shape in the longitudinal direction along the opposite ends in the width direction of the skin contact sheet 24 (i.e., SCS side end regions) 50 (50a and 50b) are regions which do not have the stretching force in the width direction and in the longitudinal direction. With this configuration, it is possible to further improve the breathability and to further suppress the skin trouble. It is further preferable that the length in the width direction of each of the SCS side end regions, which do not have the stretching force, is 2.5 to 25%, and more preferably 5 to 10%, of the width of the entire skin contact sheet (i.e., the length in the width direction of the skin contact sheet). That is, it is preferable that the sum of the lengths in the width direction of the two SCS side end regions is 5 to 50%, and more preferably 10 to 20%, of the width of the entire skin contact sheet. With the length of each of the SCS side end regions set in the above range, the balance between the close contact of the skin contact sheet with the skin of the wearer and the prevention of the skin trouble can be better maintained.

Figure 6:
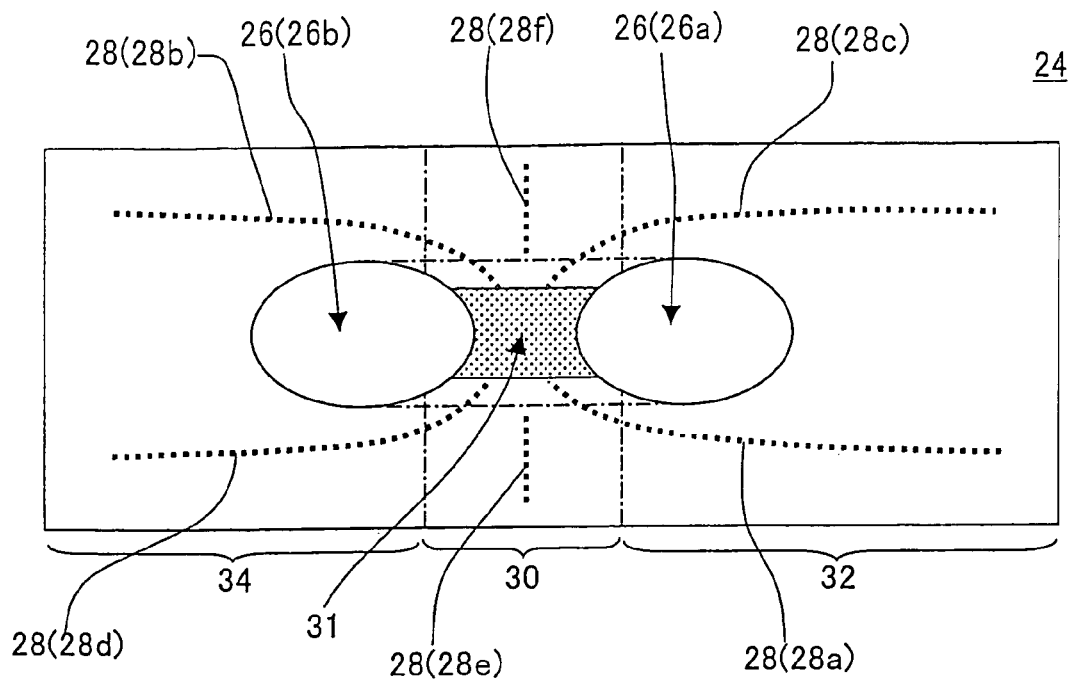
FIG. 6 is a schematic plan view illustrating the skin contact sheet used in another embodiment of the disposable diaper according to the present invention.

In addition to the structure of the skin contact sheet illustrated in FIG. 4, the skin contact sheet used in the disposable diaper according to the present invention may include a structure which has two opening stretchable members 28 (28e and 28f) extending in the width direction, as in the skin contact sheet 24 illustrated in FIG. 6, for example. As illustrated in FIG. 6, it is preferable to provide the two opening stretchable members 28 (28e and 28f) at the opposite sides in the width direction of the non-stretchable region 31, which is formed on the skin contact sheet 24 illustrated in the above FIG. 4. It is further preferable to provide the two opening stretchable members 28 (28e and 28f) along the centerline between the two openings (i.e., the urine passing opening 26a and the stool passing opening 26b).

Figure 7:
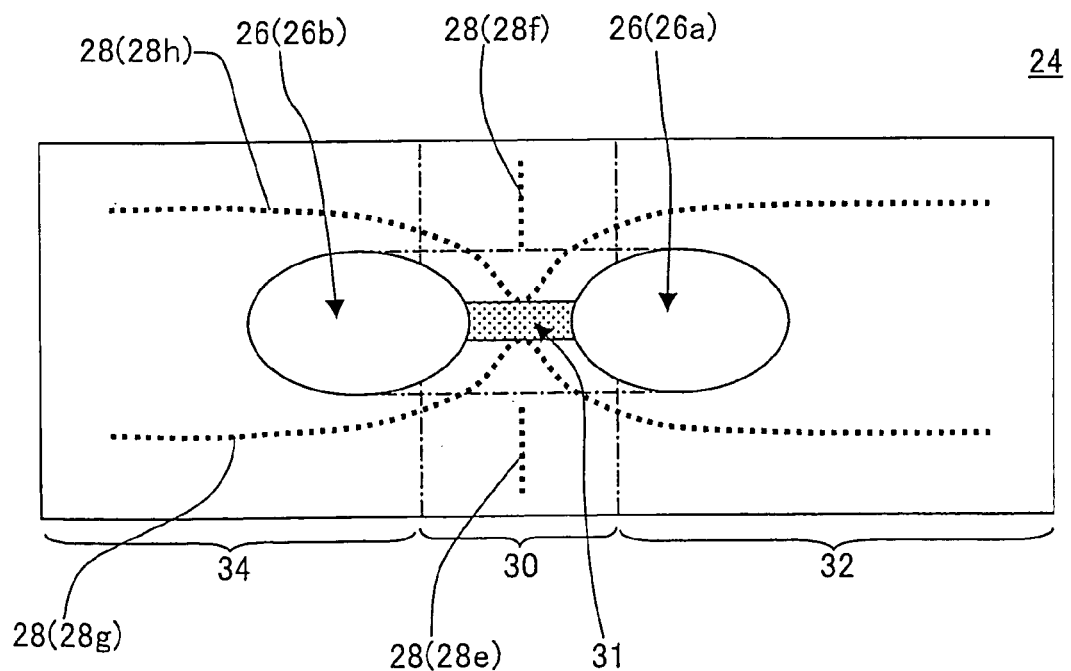
FIG. 7 is a schematic plan view illustrating the skin contact sheet used in still another embodiment of the disposable diaper according to the present invention.

Furthermore, as in the case of the skin contact sheet 24 illustrated in FIG. 7, for example, two opening stretchable members 28 (28g and 28h) may be provided to sandwich the two openings (i.e., the urine passing opening 26a and the stool passing opening 26b) from the opposite side ends of the two openings, with the two opening stretchable members 28 not crossing each other. To increase the stretching force in the width direction of the SCS central region 30, it is preferable to provide the two opening stretchable members 28 (28g and 28h) so as to bend toward the center in the width direction in the SCS central region 30 (i.e., toward the direction in which the two opening stretchable members 28 approach each other). In this case, too, the two opening stretchable members 28 (28e and 28f) extending in the width direction may be provided outside in the width direction of the bent portions.

Figure 8:
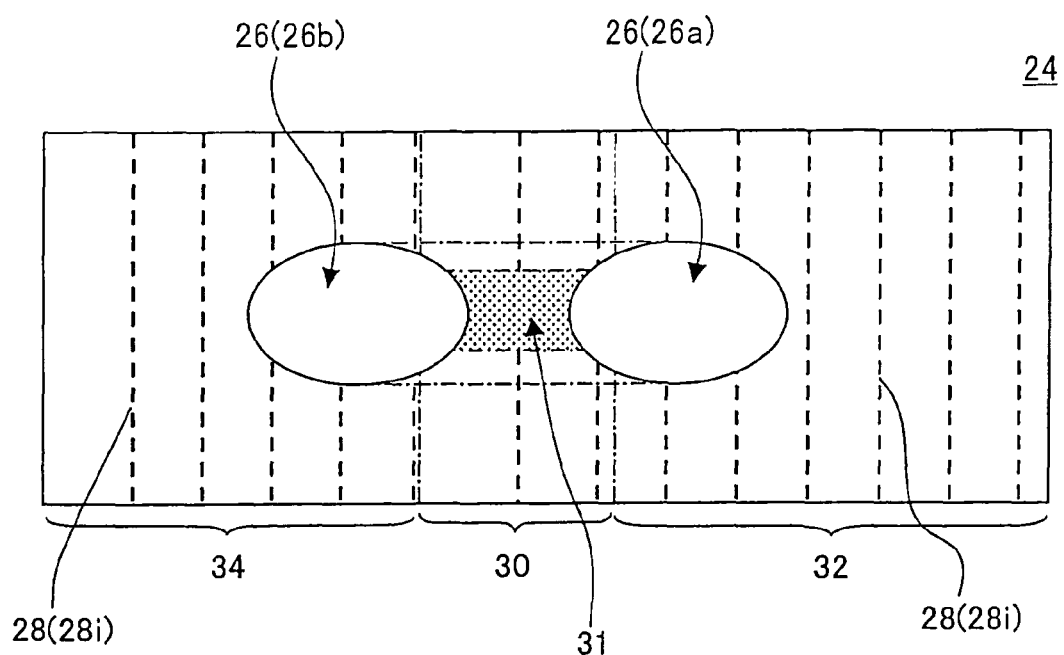
FIG. 8 is a schematic plan view illustrating the skin contact sheet used in still yet another embodiment of the disposable diaper according to the present invention.

Further, in the skin contact sheet 24 illustrated in FIG. 8, a plurality of opening stretchable members 28 (28i) extending in the width direction are provided over the entirety in the longitudinal direction of the skin contact sheet 24. In the SCS central region 30, the opening stretchable member 28i is provided with an interval formed therein. The interval portion forms the non-stretchable region 31. In the disposable diaper according to the present embodiment, the skin contact sheet 24 is thus structured. Therefore, when the disposable diaper is applied to the wearer, the non-stretchable region 31 located between the two openings (i.e., the urine passing opening 26a and the stool passing opening 26b) of the skin contact sheet 24 is not formed with a large gather and thus can be in the planar state. Accordingly, it is possible to effectively suppress the pain or the like and the skin trouble caused by the portion of the skin contact sheet corresponding to the crotch part.

The above-described arrangement pattern is preferable as the arrangement pattern of the opening stretchable members. However, there is no particular restriction on the arrangement pattern, as long as the pattern allows the SCS central region to include the non-stretchable region.

Further, if the opening stretchable members are disposed to extend in the longitudinal direction of the diaper, as illustrated in FIG. 4, the opening stretchable members are continuously arranged. This is preferable in view of an advantage that the continuous manufacture of disposable diapers can be easily performed.

If the opening stretchable members are arranged as described above, the skin contact sheet is applied with tension, and the entire skin contact sheet becomes elastic. This contributes to an advantage that the skin contact sheet can be prevented from being crushed and sinking toward the top sheet and thus can easily come into contact with the skin of the wearer. Further, with the provision of the opening stretchable members, it is possible to generate force for causing the skin contact sheet to contract and causing the top sheet, the absorber, and the back sheet to bend toward the downside (i.e., toward the exterior covering member). Therefore, the skin contact sheet can be kept spaced from the top sheet, and the skin contact sheet and the top sheet can be definitely separated from each other.

As the opening stretchable members provided on the skin contact sheet, stretchable materials used in conventional disposable diapers can be preferably used. Specifically, the stretchable materials include a rubber thread or a flat rubber string made of an elastic material such as a natural rubber or a synthetic rubber (e.g., urethane rubber), a stretchable net, a stretchable film, stretchable foam (e.g., urethane foam), and so forth.

The opening stretchable members are disposed along the openings. Thus, the contractive force in the longitudinal direction is generated around the openings. As for the contractive force in the longitudinal direction, it is preferable in the SCS dorsal region or the SCS ventral region that the contractive force in the longitudinal direction generated by each of the opening stretchable members disposed between the corresponding opening and the corresponding one of the side ends is 10 to 100 gf, and more preferably 20 to 80 gf. For example, in the SCS dorsal region 34 in FIG. 4, it is preferable that the contractive force in the longitudinal direction generated by each of the opening stretchable members 28b and 28d is in the above-described range. In this case, a segment of each of the opening stretchable members located in the SCS central region 30 is excluded from consideration. It is further preferable that the contractive force in the longitudinal direction generated by each of the opening stretchable members 28a, 28b, 28c, and 28d in the predetermined region described above (i.e., the SCS dorsal region or the SCS ventral region) is in the above-described range. With the contractive force in the longitudinal direction set in the above range, appropriate stretching force can be provided to the skin contact sheet. When the natural rubber is used, for example, it is preferable to fix a string of the natural rubber having a thickness of 0.2 to 0.25 mm and a width of 0.6 to 2.4 mm while stretching the string by 150 to 300% (i.e., 0.5 to 3 times of the natural length of the string). Further, when the urethane rubber is used, it is preferable to dispose two or three strings of the urethane rubber having a thickness of approximately 620 dtex to be in parallel to each other while stretching the strings by 200 to 300%.

The opening stretchable members as described above are fixed to the skin contact sheet with an adhesive agent or another medium. The method of fixing the opening stretchable members may be bonding with a hot-melt adhesive agent or another adhesive agent of high fluidity, or welding with heat or ultrasound such as heat-sealing, for example.

To provide sufficient stretching force to the skin contact sheet, it is preferable to fix each of the opening stretchable members while stretching the opening stretchable member so that the sheet member is formed with the gather. For example, if the opening stretchable member is the natural rubber or the synthetic rubber, it is preferable to fix the opening stretchable member while stretching the opening stretchable member by 100 to 400%, and more preferably by 200 to 300%. In particular, if the opening stretchable member is the natural rubber, it is preferable to fix the opening stretchable member while stretching the opening stretchable member by 150 to 300%, as described above. With the opening stretchable member fixed with the stretching rate of the above range, it is possible to provide the sufficient stretching force to the skin contact sheet, and more particularly to the region of the skin contact sheet excluding the SCS central region.

There is no particular restriction on the method of arranging the opening stretchable members provided on the skin contact sheet. However, as in the case of the disposable diaper 1 illustrated in FIGS. 1 to 3, for example, it is preferable to form the skin contact sheet 24 by pasting together two sheet members (i.e., an upper sheet 24a and a liner sheet 24b) between which two opening stretchable members 28 are disposed to cross in the SCS central region 30 and extend in the longitudinal direction, and to form the opening stretchable members 28a, 28b, 28c, and 28d by the snapback operation. The use of this arrangement method is preferable in that the stretching force can be provided to the skin contact sheet by the minimum necessary stretchable members.

In the disposable diaper according to the present embodiment, it is preferable to provide a separation wall for dividing the space between the skin contact sheet and the top sheet into a space communicating with the urine passing opening and a space communicating with the stool passing opening. If the urine and the stool are mixed, ammonia is generated and alkalinizes the surrounding environment. Then, an enzyme included in the stool is strongly activated in an alkaline atmosphere, and the enzyme and ammonia inflame a weakened part of the skin. Thereby, the diaper rash occurs. This mechanism is reported by Kazuya Yamamoto in Hifu Rinsho (Clinical Dermatology) 1998, vol. 30, pp 949-956. With the provision of the above-described separation wall, the urine discharged by the wearer can be absorbed and retained separately from the stool. As a result, the urine and the stool are not easily mixed, and the diaper rash can be effectively prevented.

The method of fixing the skin contact sheet includes, for example, (1) a method of fixing the skin contact sheet 24 on a surface of the top sheet 18 (or the back sheet 20), and (2) a method of fixing the skin contact sheet 24 to the inside surfaces of standing gathers, if the diaper is provided with the standing gathers.

[1-2] The absorber: The absorber is a member for absorbing and retaining the urine of the wearer. The absorber is made of an absorbent material due to the need to absorb and retain the urine and the body fluid of the wearer.

The absorbent material forming the absorber includes conventionally known absorbent materials usually used in the disposable diaper and other absorbent products, such as fluff pulp, super absorbent polymer (hereinafter referred to as SAP), and a hydrophilic sheet, for example. It is preferable to use wood pulp or non-wood pulp fibrillated into floc as the fluff pulp, to use sodium polyacrylate as the SAP, and to use tissue, an absorbent paper, or a hydrophilicized nonwoven fabric as the hydrophilic sheet.

Each of these absorbent materials is usually used in the form of a single-layer mat or a multiple-layer mat. In such a case, a single type of the above absorbent materials may be independently used, or two or more types of the absorbent materials may be used in combination. In particular, it is preferable to use approximately 10 to 500 parts by mass of the SAP with respect to 100 parts by mass of the fluff pulp. In this case, the SAP may be evenly mixed in each of the fluff pulp mats or may be disposed in layers between a plurality of fluff pulp layers.

It is necessary that the absorber is interposed between at least parts of the top sheet and the back sheet. Usually, the absorber is sandwiched between the top sheet and the back sheet, and the peripheral rim of the absorber is sealed by adhesion so that the absorber is interposed between the top sheet and the back sheet. Therefore, flap portions, in which the absorber is not interposed between the top sheet and the back sheet, are formed around the peripheral rim of the absorber.

It is preferable the entire absorber is wrapped by a hydrophilic sheet. This structure contributes to an advantage that the SAP is prevented from leaking from the absorber and the absorber is provided with the shape stability.

There is no particular restriction on the shape of the absorber. The shape of the absorber includes the shapes used in the conventional disposable diaper and other absorbent products, such as a rectangular shape, an hourglass shape, a calabash shape, and a T-shape, for example.

[1-3] The top sheet: The top sheet is a sheet disposed to cover the upper surface of the absorber (i.e., the surface at the side of the skin of the wearer when the diaper is applied to the wearer). The top sheet is at least partially (i.e., a part or the entirety of the top sheet is) made of a liquid permeable material due to the need to cause the absorber disposed at the lower surface side of the top sheet to absorb the urine of the wearer.

The liquid permeable material forming the top sheet includes a woven fabric, a nonwoven fabric, and a porous film, for example. In particular, it is preferable to use a hydrophilicized nonwoven fabric made of a thermoplastic resin such as polypropylene, polyethylene, polyester, or nylon.

The top sheet may be formed by a single sheet member. Alternatively, the top sheet may be formed by a plurality of sheet members. For example, in a frequently used embodiment of a tape-type diaper, a top sheet made of a liquid permeable material (i.e., a center sheet) is disposed at the center of the diaper, and another top sheet made of a water repellent material (i.e., a side sheet) is disposed at side flap portions of the diaper.

[1-4] The back sheet: The back sheet is a sheet disposed to cover the lower surface of the absorber (i.e., the surface at the side of the clothes of the wearer when the diaper is applied to the wearer). The back sheet is made of a liquid impermeable material due to the need to prevent the urine of the wearer from leaking to the outside of the diaper.

The liquid impermeable material forming the back sheet includes, for example, a liquid impermeable film made of a resin such as polyethylene. In particular, it is preferable to use a microporous polyethylene film. The microporous polyethylene film is formed with a multitude of micro holes of a size of 0.1 to a few micrometers. The microporous polyethylene film is liquid impermeable but moisture permeable and thus has an advantage of preventing the inside of the diaper from becoming stuffy.

A sheet member (i.e., a cover sheet) may be pasted to the outer surface of the back sheet. The cover sheet is used to reinforce the back sheet and to improve the hand feeling (i.e., the tactile feeling) of the back sheet.

The material forming the cover sheet includes a woven fabric and a nonwoven fabric, for example. In particular, it is preferable to use a dry or wet nonwoven fabric made of a thermoplastic resin such as polyethylene, polypropylene, or polyester.

[1-5] The absorbent member: In the two-piece-type and pants-type diaper, the top sheet, the back sheet, and the absorber are formed as one member, i.e., the "absorbent member" having the absorbing and retaining function. The absorbent member is joined with the exterior covering member, which has been manufactured separately from the absorbent member. Thereby, the disposable diaper is formed. In the absorbent member, as in the case of a sanitary napkin or the like, the top sheet and the back sheet are disposed on the upper surface and the lower surface of the absorber, respectively, so that the absorber is interposed between the top sheet and the back sheet. For example, the disposable diaper 1 illustrated in FIGS. 1 to 3 is an example in which the absorbent member 14 is formed by inserting the absorber 22 between the top sheet 18 and the back sheet 20 and adhering and sealing the peripheral rim of the absorber 22 to make the absorber 22 interposed between the top sheet 18 and the back sheet 20.

The absorbent member is formed into such a size to cover at least the crotch part of the diaper. To ensure the leakage preventing effect, however, it is preferable to form the absorbent member into such a size to cover not only the crotch part but also a part of the front body part and the back body part. The absorbent member can be fixed to the exterior covering member with the hot-melt adhesive agent or the like, for example.

[1-6] The exterior covering member: The exterior covering member is a member having the fitting function of covering the body of the wearer. Specifically, the exterior covering member is a sheet-shaped member for forming respective parts of the front body part, the crotch part, and the back body part.

In the two-piece-type and pants-type diaper, the absorbing and retaining function of absorbing and retaining the excrement of the wearer is performed solely by the absorbent member, and thus there is no need to use the liquid impermeable material as the material forming the exterior covering member. The material forming the exterior covering member includes, for example, a nonwoven fabric formed by a synthetic fiber of polyethylene, polypropylene, polyester, or another thermoplastic resin.

The exterior covering member is fixed, with such members as the leg-surrounding stretchable members inserted in the exterior covering member. In many cases, therefore, the exterior covering member is formed by pasting together two or more nonwoven fabrics. For example, the disposable diaper 1 illustrated in FIGS. 1 to 3 is an example in which the exterior covering member 16 is formed by two nonwoven fabrics, between which leg-surrounding stretchable members 40, waist-surrounding stretchable members 42, and belly-surrounding stretchable members 44 are inserted and fixed. FIG. 3 shows only a single nonwoven fabric of the exterior covering member 16, omitting other components.

[1-7] The respective stretchable members: In the pants-type disposable diaper, the leg-surrounding stretchable members and the waist-surrounding stretchable members are generally provided, and it is preferable to further provide the belly-surrounding stretchable members.

The leg-surrounding stretchable members are stretchable members disposed along the respective leg-surrounding openings. With the provision of the leg-surrounding stretchable members, highly stretchable gathers (i.e., leg gathers) can be formed around the leg-surrounding openings. Accordingly, a clearance gap is not easily formed around the legs, and the leakage of the urine from the leg-surrounding openings can be effectively prevented.

The waist-surrounding stretchable members are stretchable members disposed along the waist-surrounding opening. With the provision of the waist-surrounding stretchable members, a highly stretchable gather (i.e., a waist gather) can be formed around the waist-surrounding opening. With the waist gather, a clearance gap is not easily formed around the waist, and the leakage of the urine from the area around the waist can be prevented. Further, the fittedness of the diaper to the wearer is improved, and thus the diaper is prevented from slipping down.

The belly-surrounding stretchable members are stretchable members disposed in a portion between the waist-surrounding opening and the leg-surrounding openings (i.e., a portion corresponding to the area around the belly of the wearer). With the provision of the belly-surrounding stretchable members, a highly stretchable tummy gather can be formed around the belly of the wearer. Coupled with the waist gather, the tummy gather can further improve the fittedness of the diaper and the effect of preventing the slide down of the diaper.

The disposable diaper 1 illustrated in FIGS. 1 to 3 is an example in which a plurality of the leg-surrounding stretchable members 40 are disposed around the peripheral rims of the leg-surrounding openings 12*a* and 12*b*, and a plurality of the waist-surrounding stretchable members 42 are disposed around the peripheral rim of the waist-surrounding opening 10 so as to surround the waist-surrounding opening 10. Further, a plurality of the belly-surrounding stretchable members 44 are disposed in the portion between the waist-surrounding opening 10 and the leg-surrounding openings 12*a* and 12*b* (i.e., the portion corresponding to the area around the belly of the wearer) so as to surround the belly of the wearer.

Each of these stretchable members can employ a similar structure to the structure used in the above-described opening stretchable members used for the skin contact sheet. Further, the material forming the stretchable member, the elongation rate of the material, the elongated state of the stretchable member when the stretchable member is fixed, and the like can be determined in consideration of such factors as the extent of contraction of the gather.

[1-8] The standing gathers: The disposable diaper may include the standing gathers for preventing the sideward leakage of the urine discharged by the wearer. The standing gathers are members for preventing the sideward leakage of the urine discharged by the wearer, and are leakage preventing walls structured to stand three-dimensionally. With the provision of the standing gathers, even if the urine is discharged on and diffuses down the skin contact sheet, the standing gathers function as breakwaters, and the leakage from the leg-surrounding openings and the like of the diaper (i.e., the so-called "sideward leakage") can be effectively prevented. Incidentally, the word "standing gather(s)" may be expressed as "barrier cuff".

The standing gather can employ a similar structure to the structure used in the conventional disposable diaper and other absorbent products. For example, with a stretchable member (i.e., a standing gather stretchable member) provided on a part of a sheet member, a gather (i.e., folds) formed on the sheet member by the standing gather stretchable member can be preferably used.

[2] The manufacturing method: An embodiment of the method of manufacturing the disposable diaper according to the present invention will now be described, taking an example in which the disposable diaper 1 illustrated in FIGS. 1 to 3 (i.e., the two-piece-type and pants-type diaper) is manufactured.

[2-1] The manufacture of the absorbent member: The absorber 22 wrapped by a hydrophilic sheet is disposed on the upper surface of the back sheet 20, and the top sheet 18 is disposed on the upper surface of the absorber 22. Then, the peripheral rim of the absorber 22 is sealed by adhesion, sandwiched by the top sheet 18 and the back sheet 20. Thereby, the absorbent member 14 is obtained.

[2-2] The manufacture of the skin contact sheet: The upper sheet 24*a* is pasted on the upper surface of the liner sheet 24*b*, with the two opening stretchable members arranged in a predetermined pattern. The upper sheet 24*a* is formed into such a size to cover only the central region of the liner sheet 24*b* so that the opposite side ends of the liner sheet 24*b* are exposed. Further, as illustrated in FIG. 4, the two opening stretchable members are arranged in such a pattern to cross at a point between the urine passing opening 26*a* and the stool passing opening 26*b*, which are later formed, and to surround a part of the peripheral rim of each of the urine passing opening 26*a* and the stool passing opening 26*b*.

Subsequently, the urine passing opening 26*a* and the stool passing opening 26*b* are formed on the liner sheet 24*b* and the upper sheet 24*a*, which have been pasted together. Then, the crossed section of the above opening stretchable members 28 is cut and snapped back. Thereby, the opening stretchable members 28*a*, 28*b*, 28*c*, and 28*d* are formed, and the double-layer structured skin contact sheet 24 is obtained. It is preferable to fix the leading end portion of each of the thus snapped-back opening stretchable members with the adhesive agent or the like. Alternatively, another manufacturing method may be used in which the four opening stretchable members are previously provided on the upper surface of the liner sheet 24*b* and thus the snapback operation is not performed. The snapback operation may be performed prior to the formation of the urine passing opening 26*a* and the stool passing opening 26*b*.

[2-3] The provision of the skin contact sheet to the absorbent member: The skin contact sheet 24 is pasted to the surface of the top sheet 18 which forms the absorbent member 14.

[2-4] The manufacture of the exterior covering member: Two nonwoven fabrics for forming the exterior covering member 16 are first prepared. Then, the waist-surrounding stretchable members 42, the belly-surrounding stretchable members 44, and the leg-surrounding stretchable members 40 are disposed and fixed by adhesion on the upper surface of one of the nonwoven fabrics. Thereafter, the other one of the nonwoven fabrics is layered on and fixed to the upper surface of the one of the nonwoven fabrics. Thereby, the exterior covering member 16 is obtained in which the waist-surrounding stretchable members 42, the belly-surrounding stretchable members 44, and the leg-surrounding stretchable members 40 are interposed between the two nonwoven fabrics.

[2-5] The manufacture of the disposable diaper: The absorbent member 14 is disposed at and fixed to the proximity of the crotch part of the exterior covering member 16. Then, the exterior covering member 16 is folded in half such that the front body part 2 and the back body part 6 are aligned with each other, with the absorbent member 14 on the inside of the folded exterior covering member 16. Thereafter, the front body part 2 and the back body part 6 are joined by such a method as heat-sealing, so that the joining parts 8 are formed. Thereby, the disposable diaper 1 illustrated in FIGS. 1 to 3 is manufactured.

The above-described sequence of processes can be continuously performed by a mechanical method or apparatus. For example, with a method or apparatus for continuously sending out a long sheet material or a long stretching material by a roller, for example, the continuous manufacture of the disposable diaper can be performed. This contributes to the improvement of the productivity.

[3] The scope of application of the present invention: The scope of application of the disposable diaper according to the present invention is not limited to the two-piece-type and pants-type diaper described above, but the present invention is also applicable to a one-piece-type and pants-type diaper and a tape-type diaper, for example. That is, these disposable diapers can also have the effects of the disposable diaper according to the present invention, if the skin contact sheet, which is formed with the two openings and provided with the predetermined opening stretchable members, is disposed above the surface of the top sheet.

The "one-piece-type diaper" refers to a type of diaper which includes a top sheet, a back sheet, and an absorber, similarly to the two-piece-type diaper, but in which the absorber having the absorbing and retaining function is interposed (i.e., embedded) between the top sheet and the back sheet and is integrated with the top sheet and/or the back sheet having the fitting function.

The "tape-type diaper" refers to a disposable diaper which includes a top sheet, a back sheet, an absorber interposed between at least parts of the two sheets, and tape fasteners for fitting the diaper, and in which a front body part and a back body part can be fixed to each other by the tape fasteners. The "tape-type diaper" also includes the "one-piece-type" and the "two-piece-type," and the disposable diaper according to the present invention is applicable to either-type of the tape-type diaper.

The disposable diaper according to the present invention can be preferably used as the diaper for an infant or an adult such as an elder or disabled person who needs nursing care. Further, according to the disposable diaper of the present invention, the discharged stool does not easily come into direct contact with the skin of the wearer, and the stretching force of the portion of the skin contact sheet between the two openings is weak. Therefore, the disposable diaper according to the present invention can be preferably used particularly as the disposable diaper for an infant who has a sensitive skin and thus frequently has skin trouble.

What is claimed is:

1. A disposable diaper formed by a front body part, a crotch part, and a back body part, the disposable diaper comprising:
   an exterior covering member;
   an absorber provided on an inner surface of the exterior covering member;
   a top sheet disposed to cover an upper surface of the absorber and at least partially formed of a liquid permeable material;
   a back sheet disposed to cover a lower surface of the absorber and formed of a liquid impermeable material; and
   an SCS, which is a skin contact sheet, disposed above the top sheet and formed so that a portion thereof corresponds to the crotch part, wherein the skin contact sheet has an area that is sufficiently large as so to cover the top sheet, but which is smaller than an overall area of the exterior covering member, and wherein the skin contact sheet has a stool passing opening capable of passing a stool therethrough and a urine passing opening capable of passing the urine therethrough, the skin contact sheet including
      an SCS central region formed by extending an inter-opening region, which is a strip-shaped region sandwiched by the stool and urine passing openings and extending in the width direction, by half the length between the stool and urine passing openings in the anterior direction and in the posterior direction,
      an SCS ventral region located at the ventral side from the SCS central region, and
      an SCS dorsal region located at the dorsal side from the SCS central region,
      wherein at least the SCS central region of the skin contact sheet has the stretching force in the width direction, and
   wherein an inter-opening central region, which is a region located between the stool and urine passing openings, includes a non-stretchable region, which is present only between the stool and urine passing openings, and which is provided in a planar state, having no stretching force in the width direction and in the longitudinal direction.

2. The disposable diaper according to claim 1, wherein the non-stretchable region is disposed to extend into a strip shape between the stool and urine passing openings at the center in a width direction of the inter-opening central region.

3. The disposable diaper according to claim 1, wherein a length in the width direction of the non-stretchable region is 10 to 100% of a length in the width direction of the inter-opening central region.

4. The disposable diaper according to claim 2, wherein a length in the width direction of the non-stretchable region is 10 to 100% of a length in the width direction of the inter-opening central region.

5. The disposable diaper according to claim 1, wherein opening stretchable members, which are stretchable elastic members, are disposed on a region of the skin contact sheet excluding the non-stretchable region to extend in the longitudinal direction, and
wherein each of the opening stretchable members has a width-direction component at least in the SCS central region.

6. The disposable diaper according to claim 2, wherein opening stretchable members, which are stretchable elastic members, are disposed on a region of the skin contact sheet excluding the non-stretchable region to extend in the longitudinal direction, and
wherein each of the opening stretchable members has a width-direction component at least in the SCS central region.

7. The disposable diaper according to claim 3, wherein opening stretchable members, which are stretchable elastic members, are disposed on a region of the skin contact sheet excluding the non-stretchable region to extend in the longitudinal direction, and
wherein each of the opening stretchable members has a width-direction component at least in the SCS central region.

8. The disposable diaper according to claim 1, wherein the non-stretchable region of the skin contact sheet is in a planar state.

9. The disposable diaper according to claim 2, wherein the non-stretchable region of the skin contact sheet is in a planar state.

10. The disposable diaper according to claim 3, wherein the non-stretchable region of the skin contact sheet is in a planar state.

11. The disposable diaper according to claim 5, wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

12. The disposable diaper according to claim 6, wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

13. The disposable diaper according to claim 7, wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

14. The disposable diaper according to claim 8,
wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

15. The disposable diaper according to claim 9,
wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

16. The disposable diaper according to claim 10,
wherein the opening stretchable members of the skin contact sheet are formed by disposing the stretchable elastic members so as to cross between the urine passing opening and the stool passing opening and to extend in the longitudinal direction, and thereafter cutting the stretchable elastic members at the crossed section.

17. The disposable diaper according to claim 1, wherein the planar state extends substantially along the entirety of the non-stretchable region.

* * * * *